(12) United States Patent
Ludwin et al.

(10) Patent No.: US 9,402,556 B2
(45) Date of Patent: Aug. 2, 2016

(54) COMPENSATION FOR HEART MOVEMENT IN A BODY COORDINATE SYSTEM

(75) Inventors: Doron Moshe Ludwin, Haifa (IL); Eliahu Zino, Atlit (IL); Masha Nikolski, Haifa (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 13/493,151

(22) Filed: Jun. 11, 2012

(65) Prior Publication Data

US 2013/0331717 A1    Dec. 12, 2013

(51) Int. Cl.
| | | |
|---|---|---|
| A61B 5/04 | (2006.01) |
| A61B 5/042 | (2006.01) |
| A61B 5/00 | (2006.01) |
| A61B 5/06 | (2006.01) |
| A61B 17/00 | (2006.01) |

(52) U.S. Cl.
CPC .............. *A61B 5/0422* (2013.01); *A61B 5/065* (2013.01); *A61B 5/068* (2013.01); *A61B 5/6852* (2013.01); *A61B 2017/00703* (2013.01); *A61B 2034/2072* (2016.02)

(58) Field of Classification Search
CPC ............. A61B 2017/00703; A61B 2019/5251; A61B 2019/5272; A61B 19/5244; A61B 5/0422; A61B 5/6852; A61B 5/068; A61B 5/065
USPC ........................................................ 600/513
See application file for complete search history.

(56) References Cited

U.S. PATENT DOCUMENTS

| | | | |
|---|---|---|---|
| 6,024,739 A | 2/2000 | Ponzi et al. | |
| 6,716,166 B2 | 4/2004 | Govari | |
| 6,773,402 B2 | 8/2004 | Govari et al. | |
| 7,848,789 B2 | 12/2010 | Govari et al. | |
| 2003/0074011 A1 | 4/2003 | Gilboa et al. | |
| 2010/0268059 A1* | 10/2010 | Ryu et al. ...................... 600/407 |
| 2011/0066203 A1* | 3/2011 | Rosenberg et al. ............. 607/17 |

FOREIGN PATENT DOCUMENTS

| | | |
|---|---|---|
| EP | 0911059 A2 | 4/1999 |
| EP | 1743575 A2 | 1/2007 |
| EP | 2000098 A2 | 12/2008 |
| WO | WO 97/25101 A2 | 7/1997 |
| WO | WO 02/082375 A2 | 10/2002 |

OTHER PUBLICATIONS

European Search Report dated Aug. 12, 2015 for corresponding Application No. EP13171290.3.

* cited by examiner

*Primary Examiner* — Niketa Patel
*Assistant Examiner* — Lindsey G Hankins
(74) *Attorney, Agent, or Firm* — Louis J. Capezzuto

(57) ABSTRACT

A method, including inserting a flexible probe into a living subject and positioning a distal end of the probe in a heart of the subject, the distal end including a position sensor configured to generate position signals indicative of a position of the distal end, and an electrode configured to convey electrical signals from the heart. The method further includes formulating, in response to the position signals, a first indication of a change in a mean position of the heart within the living subject and deriving a second indication of a change in the electrical signals. The method also includes determining, in response to the first and second indications, a new mean position of the heart.

24 Claims, 6 Drawing Sheets

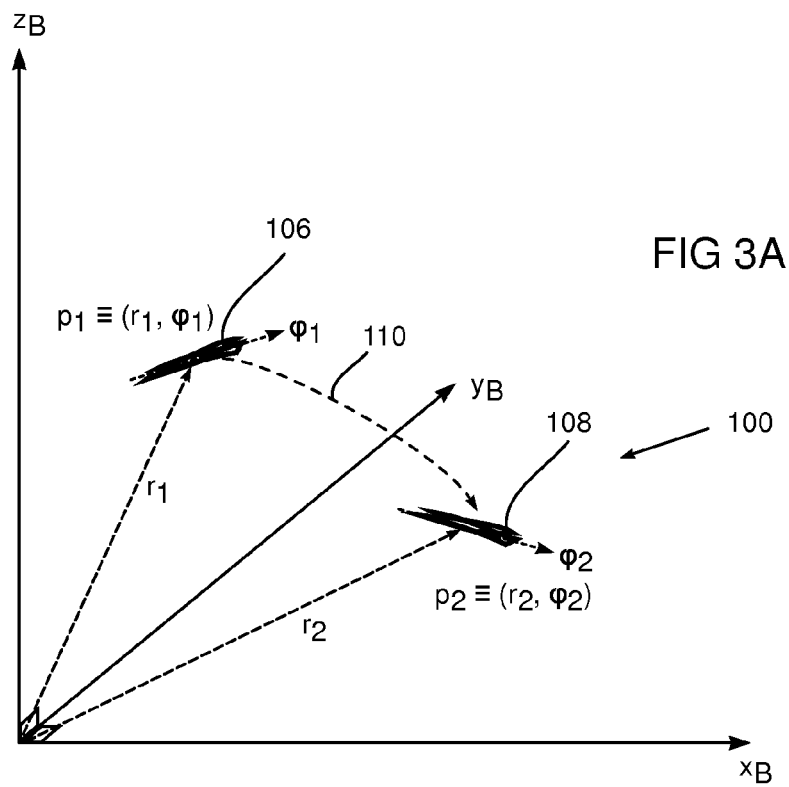
FIG 3A
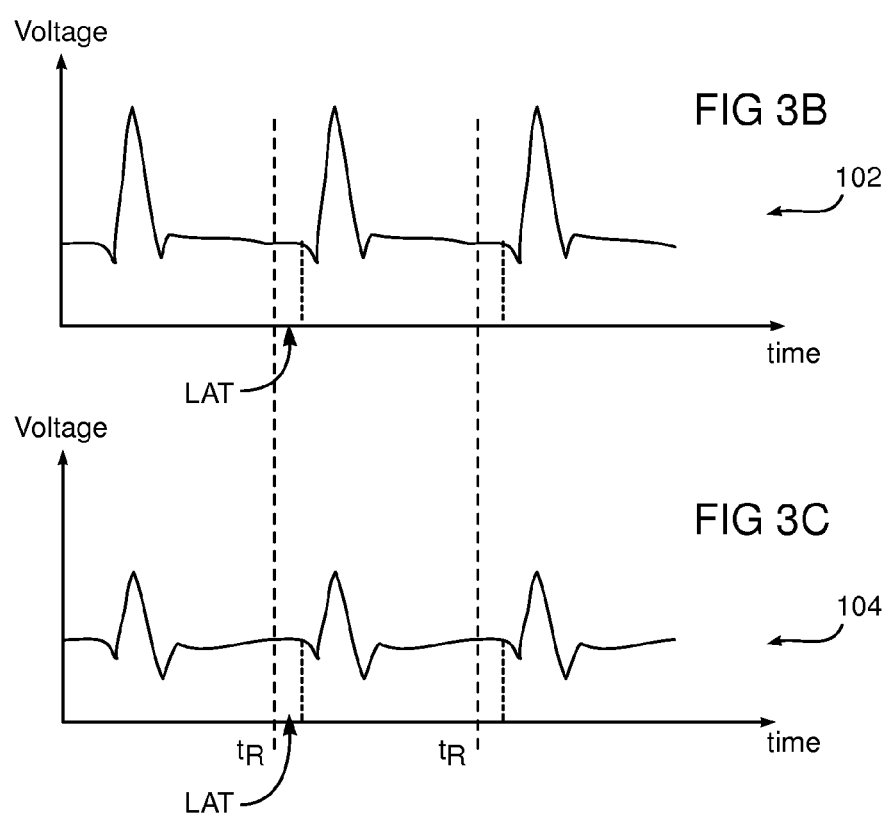
FIG 3B
FIG 3C

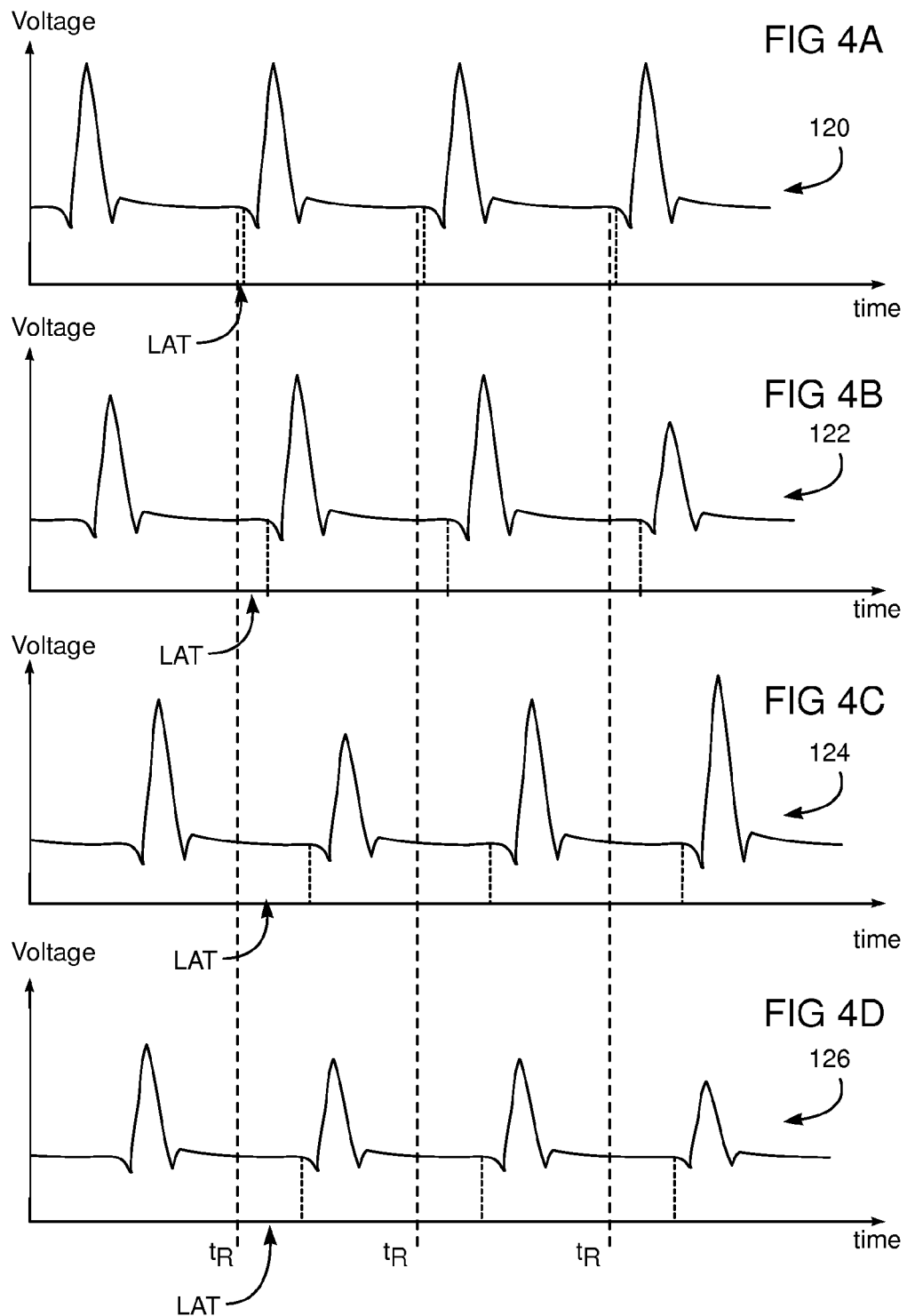

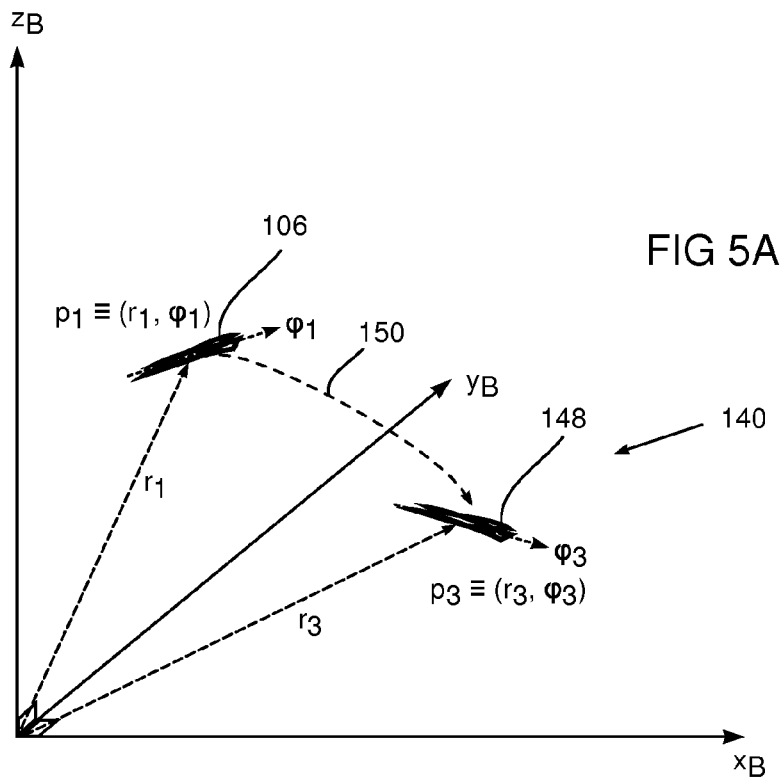
FIG 5A
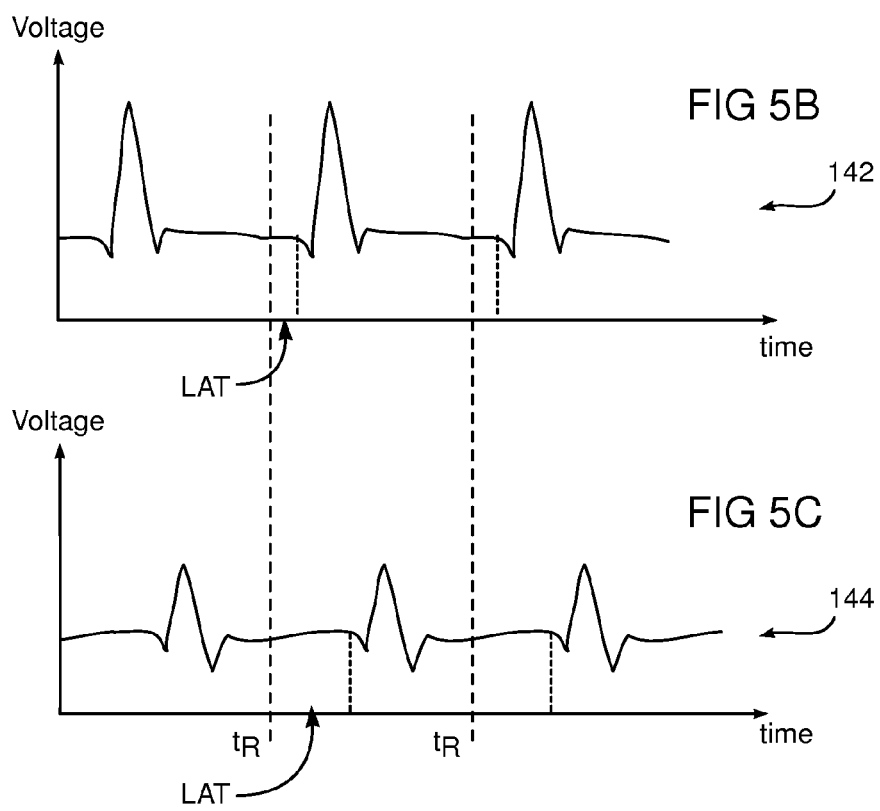
FIG 5B
FIG 5C

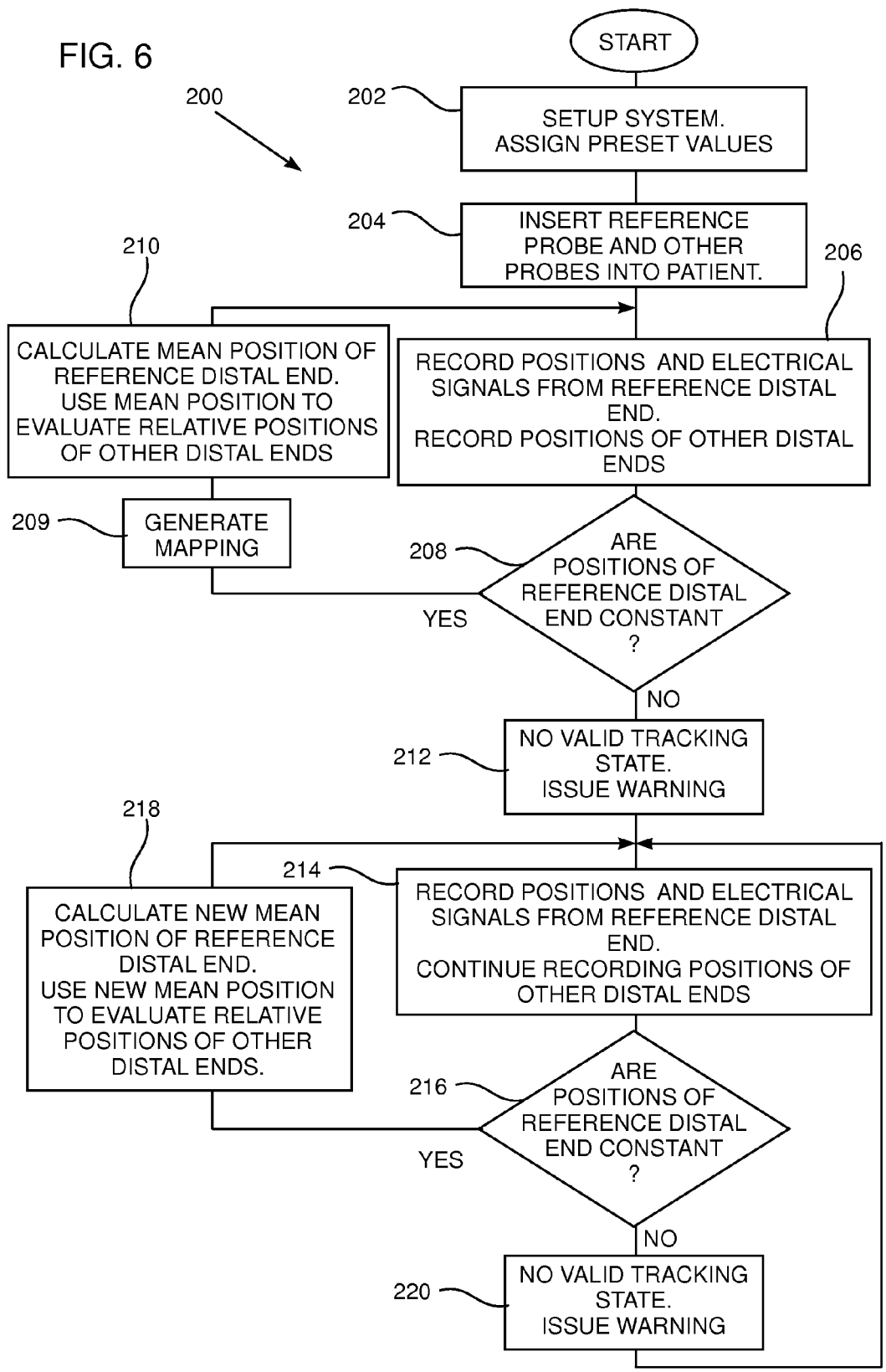

COMPENSATION FOR HEART MOVEMENT IN A BODY COORDINATE SYSTEM

FIELD OF THE INVENTION

The present invention relates generally to electrocardiography, and specifically to tracking a probe used in an electrocardiography procedure.

BACKGROUND OF THE INVENTION

A critical need during electrocardiography, wherein probes are positioned within the heart, is accurate tracking of the probes. Any method to improve the tracking is advantageous.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

inserting a flexible probe into a living subject;

positioning a distal end of the probe in a heart of the subject, the distal end including a position sensor configured to generate position signals indicative of a position of the distal end, and an electrode configured to convey electrical signals from the heart;

formulating, in response to the position signals, a first indication of a change in a mean position of the heart within the living subject;

deriving a second indication of a change in the electrical signals; and determining, in response to the first and second indications, a new mean position of the heart.

Typically the change in the mean position of the heart is responsive to a change in the position of the distal end.

In a disclosed embodiment the position of the distal end includes a mean position of the distal end measured during a preset number of heart beats of the heart. Typically, formulating the first indication includes determining that the position of the distal end does not correspond to the mean position.

In a further disclosed embodiment the second indication is derived in response to determining that the change in the mean position is a non-zero change.

In a yet further disclosed embodiment the second indication is indicative of no change in the electrical signals.

In an alternative embodiment the electrode consists of a plurality of electrodes attached to the distal end, and the plurality of electrodes are configured to convey respective electrical signals from respective sites in the heart. The method may include formulating a mapping between respective parameters of the respective electrical signals and respective positions of the respective sites. The method may also include positioning a further distal end of a further probe in the heart, and determining a further position of the further distal end in response to the mapping.

The respective parameters may include respective local activation times of the respective electrical signals, and the method may include determining a change in the position of the distal end in response to the mapping.

In a further alternative embodiment the method includes positioning a further distal end of a further probe in the heart, and determining a further position of the further distal end in response to the new mean position of the heart.

There is further provided, according to an embodiment of the present invention, apparatus, including:

a flexible probe, having a distal end, configured to be inserted into a living subject;

a position sensor included in the distal end, configured to generate position signals indicative of a position of the distal end in a heart of the subject;

an electrode included in the distal end, configured to convey electrical signals from the heart; and a processor, configured to:

formulate, in response to the position signals, a first indication of a change in a mean position of the heart within the living subject, derive a second indication of a change in the electrical signals, and determine, in response to the first and second indications, a new mean position of the heart.

The present disclosure will be more fully understood from the following detailed description of the embodiments thereof, taken together with the drawings, in which:

BRIEF DESCRIPTION OF THE DRAWINGS

FIG. 3A is a schematic graph illustrating the motion of a reference distal end of the probe, and FIGS. 3B and 3C are schematic graphs illustrating signals derived from an electrode on the distal end, according to embodiments of the present invention;

FIGS. 4A-4D are schematic graphs of intrabody electrical signals, according to embodiments of the present invention;

FIG. 5A is a schematic graph illustrating the motion of the reference distal end, and FIGS. 5B and 5C are schematic graphs illustrating signals derived from the electrode on the distal end, according to alternative embodiments of the present invention; and FIG. 6 is a flowchart showing steps performed in operating the system, according to an embodiment of the present invention.

DETAILED DESCRIPTION OF EMBODIMENTS

Overview

An embodiment of the present invention provides a system and method for tracking a distal end of a reference probe within the heart of a living subject. Typically the tracked distal end may be used as a reference for tracking distal ends of other probes in the heart.

The reference distal end comprises a position sensor and an electrode attached to the distal end. After insertion of the reference distal end to a reference site of the heart, typically comprising the coronary sinus, a processor records position signals from the sensor and intrabody electrical signals from the electrode. The processor monitors the position signals as the heart beats. Providing the signals are repetitive over a preset number of heart beats, so that there is substantially no change in a mean position of the reference distal end, the processor uses the mean position as a mean position of the heart.

If the position signals register a change in the position of the reference distal end, the processor waits until the signals again become repetitive, and uses the new mean position of the distal end as a new mean position of the heart.

Typically, the change registered by the position signals may be caused by a change in a body frame of reference used to measure the positions, and/or by a movement of the reference distal end with respect to its reference site. Embodiments of the present invention correct for both causes. Changes in the body frame of reference are corrected for using the mean position measurements described above. Changes because of reference distal end movement may be corrected for by generating a mapping between the intrabody electrical signals and different reference sites to where the distal end may move. In the event of distal end movement, the mapping may be used to estimate a position of a new reference site.

The position of the reference distal end may be used as a reference for other probe distal ends positioned in the heart. Such a use averts recalibration of the body frame of reference, which in prior art systems is necessary if sensors defining the frame have changed. The use also corrects for overall movement of the heart in the thoracic cavity, such as may occur during defibrillation of the heart.

System Description

Figure 1:
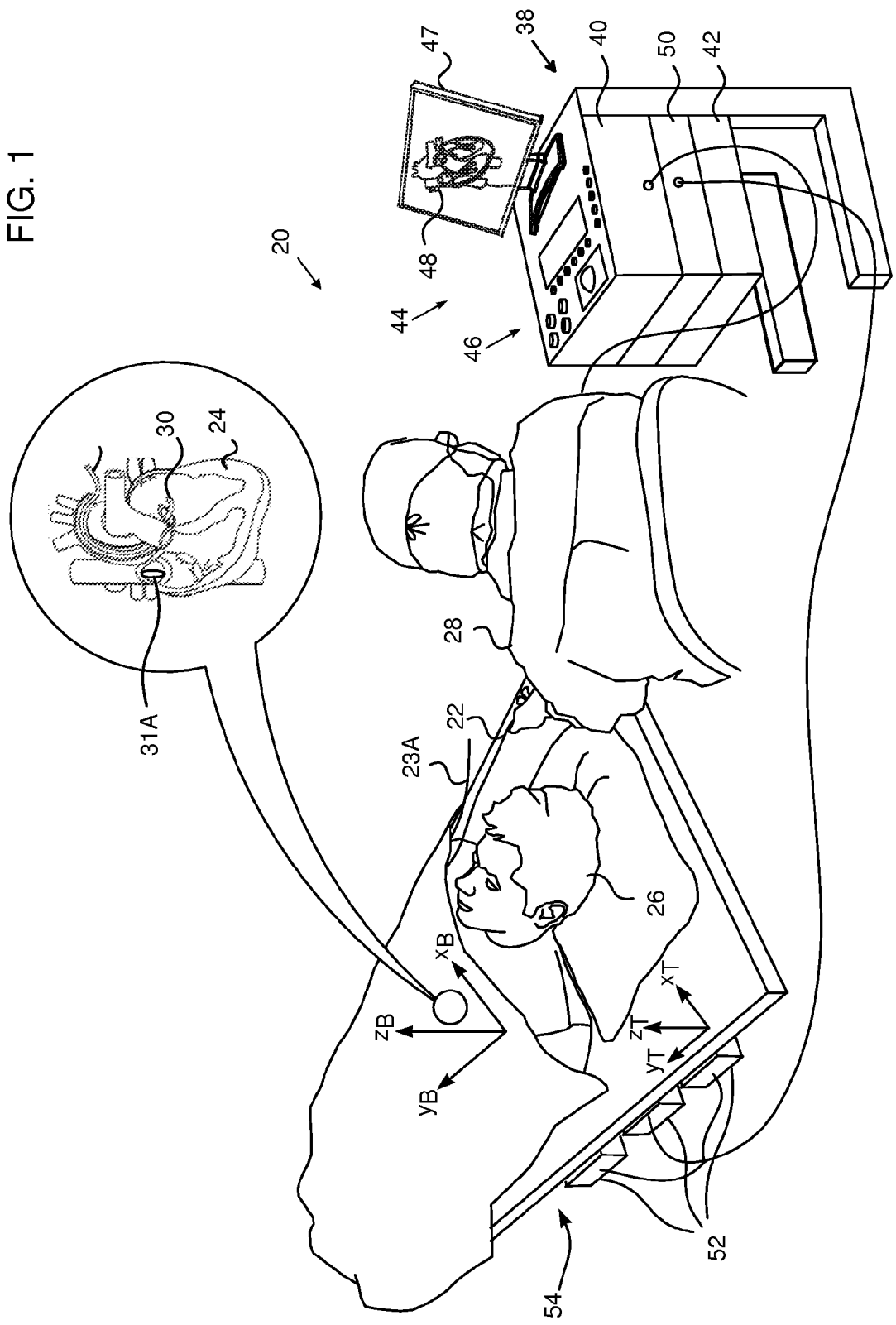
FIG. 1 is a schematic illustration of a heart movement compensation system, according to an embodiment of the present invention.
Figure 2:
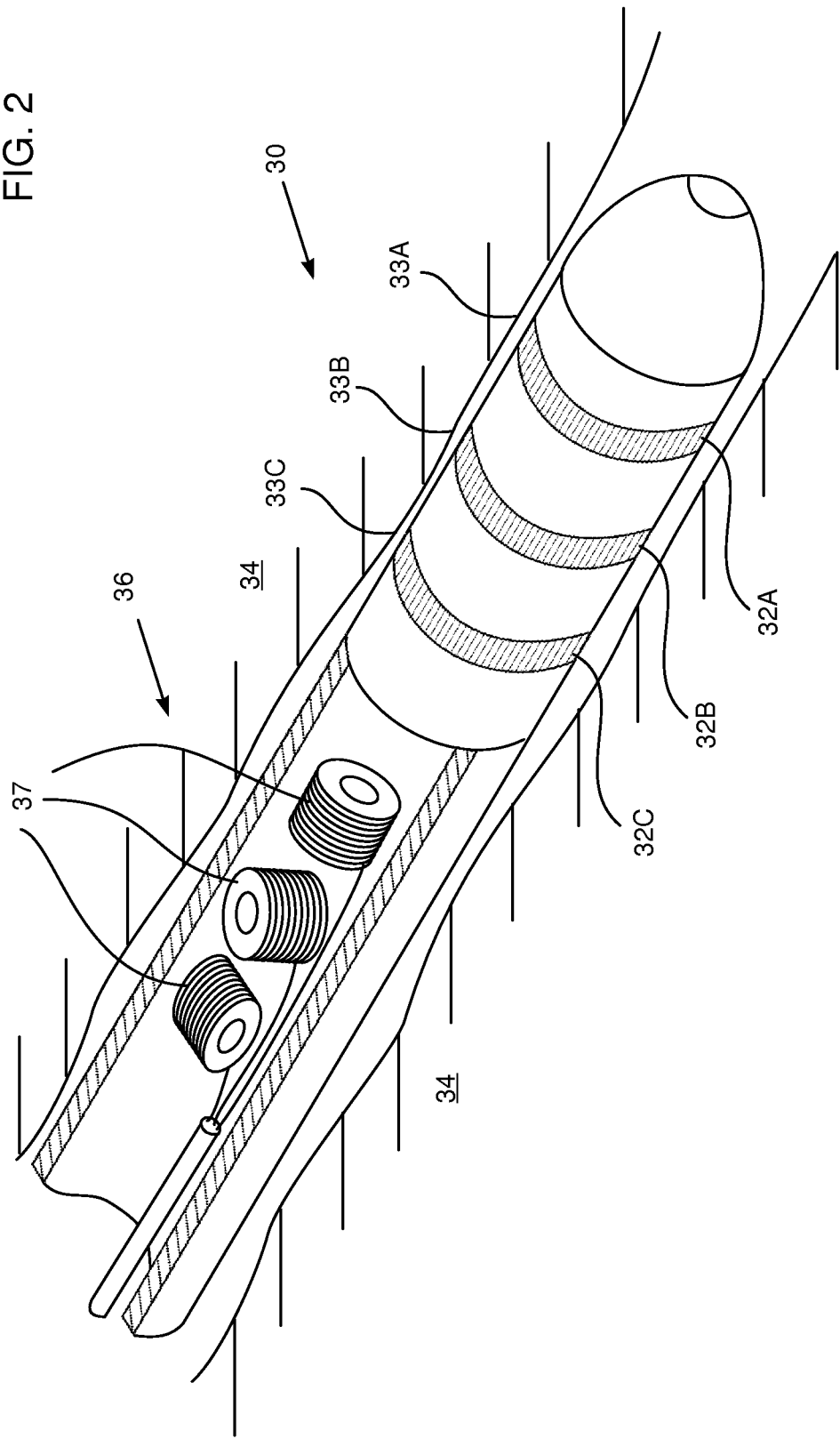
FIG. 2 is a schematic illustration of a distal end of a probe used in the system, according to an embodiment of the present invention.

Reference is now made to FIG. 1, which is a schematic illustration of a heart movement compensation system 20, and to FIG. 2, which is a schematic illustration of a distal end of a probe 22 in system 20, according to embodiments of the present invention. For simplicity and clarity, the following description assumes that system 20 operates while a medical procedure is performed on a heart 24, herein assumed to comprise a human heart, using probe 22. System 20 includes facilities for tracking probe 22, as well as for receiving electrical signals, also herein termed intrabody electrocardiograph (ECG) signals, detected by the probe. System 20 typically includes other facilities used during the medical procedure, such as a facility for ablating one or more regions of heart 24.

Probe 22 comprises a catheter which is inserted into the body of a subject 26 during the medical procedure. The medical procedure is performed by a user 28 of system 20, and in the description herein user 28 is assumed, by way of example, to be a medical professional. A distal end 30 of the probe comprises a plurality of generally similar electrodes 32A, 32B, 32C, . . . , collectively referred to herein as electrodes 32. Electrodes 32A, 32B, 32C, . . . , receive electrical signals from respective sites 33A, 33B, 33C, . . . in the heart of the subject, and the signals are analyzed by system 20, as described herein. Distal end 30 is assumed to be positioned within a blood vessel 34 of heart 24.

Distal end 30 comprises a position sensor 36, which is assumed herein to comprise one or more coils 37 providing signals which vary according to the position, i.e., the location and orientation, of the distal end. The operation of sensor 36 is described in more detail below.

In addition to probe 22, professional 28 also uses probes 23A, 23B, . . . collectively referred to herein as probes 23, during the medical procedure. Probes 23 are generally similar in construction and operation to probe 22, and have respective distal ends 31A, 31B, . . . collectively referred to herein as distal ends 31. For simplicity only probe 23A and distal end 31A are shown in FIG. 1.

System 20 is typically controlled by a system processor 38 which may be realized as a general purpose computer. The system processor comprises a processing unit 40 communicating with a memory 42. Processor 38 may be mounted in a console 44, comprising operating controls 46 that typically include a keypad and a pointing device such as a mouse or trackball that professional 28 uses to interact with the processor. Results of the operations performed by processor 38 are provided to the professional on a screen 47 which displays a diagram 48 of results generated by system 20. The screen typically displays other items of auxiliary information related to the heart while the heart is being investigated, such as the positions of distal end 30, and the positions of other catheters used by professional 28. Screen 47 typically also presents a graphic user interface to the professional. Professional 28 is able to use controls 46 to input values of parameters used by processor 38 in the operation of system 20.

Processor 38 uses computer software, including a probe tracker module 50, to operate system 20. The software may be downloaded to processor 38 in electronic form, over a network, for example, or it may, alternatively or additionally, be provided and/or stored on non-transitory tangible computer-readable media, such as magnetic, optical, or electronic memory.

Probe tracker module 50 tracks distal end 30 while the probe is within subject 26. The tracker module typically tracks both the location and the orientation of the distal end of the probe, within the heart of subject 26. In some embodiments module 50 tracks other sections of the probe. While the tracker module may use any method for tracking probes known in the art, using an appropriate position sensor, in the present description for clarity and simplicity module 50 is assumed to comprise a magnetic tracker, such as the Carto® system produced by Biosense Webster, of Diamond Bar, Calif. Module operates magnetic field transmitters 52 in the vicinity of subject 26, so that magnetic fields from the transmitters interact with tracking coils 37 located in distal end 30.

The coils interacting with the magnetic fields generate signals which are transmitted to the module, and the module analyzes the signals to determine a location and orientation of distal end 30. Alternatively or additionally, tracker module 50 may track the distal end of probe 22 by measuring impedances between one or more of electrodes 32 and electrodes on the skin of subject 26. (In this case electrodes 32 also act as the position sensor, being used for both intrabody ECG detection and for tracking.) The Carto3® system produced by Biosense Webster uses both magnetic field transmitters and impedance measurements for tracking. U.S. Pat. No. 7,848,789, to Govari et al., whose disclosure is incorporated herein by reference, describes using both magnetic fields and impedance measurements for probe tracking.

By generally similar methods as those used for tracking distal end 30, probe tracker module 50 also tracks the locations and orientations of distal ends 31. As explained further below, distal end 30 of probe 22 is typically used as a reference for tracking of distal ends 31, so that probe 22 is also referred to herein as reference probe 22, and distal end 30 is also referred to herein as reference distal end 30.

Transmitters 52 are fixed, and define a transmitter frame of reference in terms of a first set of orthogonal axes $x_T$, $y_T$, $z_T$ which are fixed with respect to the transmitters. However, while the signals derived from sensor 36 and the sensors of probes 23 provide coordinates of the location and orientation of distal end 30 and distal ends 31 with respect to the transmitter frame of reference, professional 28 typically requires knowledge of the location and orientation of the distal ends with respect to subject 26. In order to provide this latter location and orientation, a set of patient position sensors 54, generally similar to sensor 36, are attached to the skin of subject 26. Typically sensors 54 are attached to known locations on the back of the subject. Module 50 receives signals from sensors 54, and uses the signals to define a body coordinate frame of reference in terms of a second set of body coordinate orthogonal axes $x_B$, $y_B$, $z_B$ which are fixed with respect to subject 26. As described below, during a procedure processor 38 registers the two frames of reference, and so is able to generate the location and orientation of the distal ends with respect to the subject.

FIG. 3A is a schematic graph illustrating the motion of reference distal end 30, and FIGS. 3B and 3C are schematic graphs illustrating signals derived from one of the electrodes on the distal end, according to embodiments of the present invention. A graph 100 illustrates the motion plotted spatially on body coordinate axes $x_B$, $y_B$, $z_B$. As stated above, probe 22 is assumed to be used as a reference probe, so that professional 28 places reference distal end 30 of the probe in a known position within heart 24, herein assumed to be within the coronary sinus of the heart. Once placed, professional 28 does not move distal end 30, and except as described hereinbelow, the reference distal end is assumed to remain substantially fixed within the coronary sinus. It will be understood that system 20 may use positions of distal end 30 to determine positions of heart 24, so that, for example, a mean position of the distal end corresponds to a mean position of the heart.

Within the coronary sinus, (or within any other reference position within heart 24) distal end 30 moves according to the beating of heart 24. During the procedure on heart 24, processor 38 uses signals from position sensor 36 to measure positions, i.e., locations and orientations, of the distal end. Because of the beating of the heart, locations r and orientations $\phi$ of the reference distal end taken over a period of time repeat spatially, as illustrated schematically by overlapping graph lines 106. The occurrence of a substantially repetitive nature of the reference distal end motion, typically over a preset number of heart beats, defines a valid system tracking state. During such a valid system tracking state distal end positions p are assumed to vary about a mean position $p_1$. Equation (1) is an identity for mean position $p_1$:

$$p_1 \equiv (r_1, \phi_1) \qquad (1)$$

where $r_1$ is a mean location of the reference distal end in heart 24, and $\phi_1$ is a mean orientation of the reference distal end in the heart.

The situation illustrated by lines 106 is after processor 38 has registered the body frame of reference with the transmitter frame of reference. The illustrated situation typically exists while the frames of reference registration is valid, and also while the valid system tracking state (i.e., that the reference distal end moves repetitively) exists. While a valid frames of reference registration exists, as illustrated by lines 106, processor 38 may use distal end 30 as a reference for valid tracking of distal ends 31, by evaluating relative position vectors between distal ends 31 and reference distal end 30. (For simplicity, distal ends 31 and the relative position vectors to distal ends 31 from reference distal end 30 are not shown in the diagram.)

The frames of reference registration exemplified by lines 106 typically continues to be valid unless there is a movement of position sensors 54 with respect to transmitters 52. Even if the registration of the two frames of reference remains valid, other factors, such as movement of heart 24 within patient 26 (due, for example, to the patient being defibrillated), may invalidate the tracking of distal end 30, and thus, since distal end 30 is used as a reference, the tracking of distal ends 31.

As described below, embodiments of the present invention check if the tracking of reference distal end 30 has changed, and provide a method for system 20 to correct for any such changes.

Overlapping lines 108 depict a situation where the tracking of reference distal end 30 has changed, and a new valid tracking state of the distal end exists. The change may be because of a movement of the body frame of reference, so that the body frame of reference depicted in FIG. 3A is no longer applicable; alternatively or additionally, the change may be because of a movement of the heart within the thoracic cavity. In both cases, the mean position of the reference distal end changes, from its initial value $p_1$ to a new value $p_2$, as illustrated in FIG. 3A. Equation (2) is an identity for mean position $p_2$:

$$p_2 \equiv (r_2, \phi_2) \qquad (2)$$

where $r_2$ is a mean location of the reference distal end during the second valid tracking state, and $\phi_2$ is a mean orientation of the reference distal end in the second state.

The transfer between the two valid tracking states of the distal end is indicated schematically by a broken arrow 110.

A change from a valid tracking state may also occur because of a movement of reference distal end 30 within heart 24. Such a movement may happen, even if professional 28 has not moved the proximal end of probe 22, for example due to defibrillation. Embodiments of the present invention check if reference distal end 30 has moved within the heart. In the event of such movement, an embodiment of the present invention measures and provides a correction for the movement, as described below.

While processor 38 measures the position of distal end 30 using sensor 36, it also records the intrabody electrical signals received from electrodes 32. Graphs 102 and 104 illustrate the signals received from single electrode 32B. The signals are plotted as potential vs. time graphs, received respectively during the period within which lines 106 are generated (graph 102), and during the period within which lines 108 are generated (graph 104).

The two graphs show the signals compared to a reference parameter, typically generated by the processor using skin ECG signals that are recorded simultaneously with the intracardiac signals from electrodes 32. For simplicity and clarity, in the description herein the reference parameter is assumed to comprise a local activation time (LAT) of the intrabody signals measured with respect to a reference time $t_R$. However, any other convenient reference parameter, such as a phase of the signals, a time of occurrence of the R peak of the QRS complex, an amplitude of the peak, or a combination of such parameters, may be used as a reference parameter. Processor 38 applies the reference parameter in order to quantitatively compare sequential intrabody electrical signals.

The LAT of the intrabody electrical signals is dependent on the position of electrodes 32 in heart 24. As is illustrated by graphs 102 and 104, there is no change of LAT between the two graphs. Because there is no change of LAT between graphs 102 and 104, distal end 30 has not moved within heart 24, and so is at its initial site within coronary sinus of the heart, as placed by professional 28. Thus, processor 38 is able to use the new reference distal end mean position value, $p_2$, as a reference for the initial site within the coronary sinus. In addition, using the new mean position $p_2$ as a reference, the processor is able to continue to track the positions, i.e., the locations and orientations, of distal ends 31, by applying the relative position vectors between distal ends 31 and reference distal end 30 recorded before the change in valid tracking states.

FIGS. 4A-4D are schematic graphs of intrabody electrical signals, according to embodiments of the present invention. Graphs 120, 122, and 124 respectively illustrate the signals conveyed from electrodes 32A, 32B, and 32C to processor 38 (FIGS. 1 and 2). As stated above, the respective signals are generated by respective sites 33A, 33B, 33C in heart 24, and the sites are assumed to be within the coronary sinus. While the graphs illustrate that signals generated at the different sites are generally similar in morphology and in period, because of the different physical locations of the sites, there are differences, such as different levels of particular sections of the signals, and/or differences in phase.

Processor 28 can record the signals from different sites, and can generate and store a mapping between the different signals and the different sites generating the signals. For clarity and simplicity in the following description, the mapping is assumed to comprise a mapping between respective LATs and site locations, and those having ordinary skill in the art will be able to modify the description, mutatis mutandis, for other types of mapping. Thus, as illustrated in the graphs, the LAT increases from site 33A (graph 120), to site 33B (graph 122) to site 33C (graph 124).

Processor 28 is able to use the mapped LATs to identify if distal end 30 has moved relative to sites 33A, 33B, and 33C. If there has been no movement, then the electrode signals are generally unchanged, as exemplified above for graphs 102 and 104 (FIGS. 3B, 3C).

Graph 126 (FIG. 4D) is a graph of signals from electrode 32B, assumed to be recorded at a time different from the time of recording of graph 122. The LAT of the signals of graph 126 is larger than the LAT of graph 122, indicating that electrode 32B, and thus distal end 30, has moved relative to sites 33A, 33B, and 33C. Processor 28 quantifies the movement by using the stored mapping, described above. Thus, since the LAT of graph 126 lies between the LATs of graphs 122 and 124, corresponding to regions 33B and 33C, processor 28 can determine by interpolation the new site location, between sites 33B and 33C, of electrode 33B.

In general, from the stored mapping between signals and electrode locations described above, processor 28 can use interpolation and/or extrapolation to determine a new location for a given electrode, and thus a new location of the electrode's distal end, from the new intrabody electrical signals generated at the electrode. Furthermore, while the description above has referred to determining a new location for the distal end, a similar method, which will be apparent to those having ordinary skill in the art, mutatis mutandis, may be used to determine a new orientation of the distal end from the new intrabody electrical signals. Thus, the new intrabody electrical signals may be used to find a new position, i.e., a new location and a new orientation, of the reference distal end.

FIG. 5A is a schematic graph illustrating the motion of reference distal end 30, and FIGS. 5B and 5C are schematic graphs illustrating signals derived from one of the electrodes on the distal end, according to alternative embodiments of the present invention. Apart from the differences described below, a graph 140 of FIG. 5A is generally similar to graph 100 (FIG. 3A), and elements indicated by the same reference numerals in the graphs are generally similar in property. Graphs 140 and 100 both illustrate the motion of reference distal end 30 plotted spatially on body coordinate axes $x_B$, $y_B$, $z_B$. A graph 142 of FIG. 5B is generally similar to graph 102 (FIG. 3B). Both graphs illustrate intrabody electrical signals derived from one of the electrodes on the distal end, herein assumed to be electrode 32B, during a first valid system tracking state illustrated by lines 106.

In contrast to the situation illustrated in FIGS. 3A-3C, where there is no movement of distal end 30 within heart 24 as the end transfers between two valid system tracking states, in the situation illustrated in FIGS. 5A-5C, there is movement of distal end 30 within heart 24. As illustrated in FIG. 5A, distal end 30 transfers from a first valid state, illustrated by overlapping lines 106 and having a mean position $p_1$ defined by equation (1). The transfer is to a new valid tracking state, illustrated by overlapping lines 148, having a mean position $p_3$ defined by equation (3):

$$P_3 = (r_3, \phi_3) \qquad (3)$$

where $r_3$ is a mean location of the reference distal end during the new valid tracking state, and $\phi_3$ is a mean orientation of the reference distal end in the new state.

The transfer to the new valid tracking state is indicated schematically be a broken arrow 150.

Graph 144 is a graph of the signals from electrode 32B taken during the new valid tracking state. As illustrated in graphs 142 and 144, there is a change in LAT between the two sets of signals: the LAT of graph 144 is larger than the LAT of graph 142. Thus, by measuring the LATs, processor 38 is able to deduce that distal end has moved. In addition, as explained above with reference to FIGS. 4A-4D, from the values of the LATs of graphs 142 and 144, the processor is able to quantify the movement using the stored mapping, based on signals from electrodes 32A, 32B, 32C, . . . .

FIG. 6 is a flowchart 200 showing steps performed in operating system 20, according to an embodiment of the present invention. In a system setup step 202, professional 28 attaches position sensors 54 to subject 26 and activates transmitters 52. Processor 38 then uses module 50 to formulate a body coordinate frame of reference. Professional 28 may also select a value for the number of heart beats to be used as a preset value for system 20 to use in deciding if a valid system tracking state exists. A typical value is 10, although any other convenient number may be selected. In setup step 202 the professional typically sets other preset values to be used in the flowchart. In addition, the professional defines the parameter to be used in checking if signals from electrodes 32 have changed. For simplicity, in the description of the flowchart the parameter is assumed to be the LAT of the signals.

In a probe insertion step 204, professional 28 inserts reference probe 22 into subject 26 until reference distal end 30 is in a selected site within a desired reference region, herein assumed to comprise the coronary sinus. In addition, as required, the professional inserts other probes 23 into subject 26, until the distal ends of the other probes are also in desired regions. The distal end positions are calculated by processor 38 and module 50, and are typically displayed to the professional numerically and/or graphically on screen 47.

In a first recording step 206, the processor records the positions of reference distal end 30 over a time interval. The processor uses the positions of the reference distal end to provide a position for heart 24. During the same time interval the processor also records electrical signals from electrodes 32. In addition, the processor records the positions of distal ends 31 of other probes 23. The recordings are made for the preset number of heart beats.

In a first decision step 208, processor 38 checks if the positions of reference distal end 30 recorded in step 206 are repetitive, so that over the recording time interval the positions are substantially constant. The check for repetitiveness may be by any convenient means, for example by checking that the average position of the distal end, calculated for each heart beat, does not vary by more than a preset range.

If the positions do repeat, then in a mapping step 209 the processor generates a mapping between the LATs of the electrical signals of electrodes 32, and positions of the respective sites within the heart which the electrodes contact. The positions of the sites may be determined from known dimensions of reference distal end 30 and its electrodes, as well as from the position of the reference distal end as recorded in step 206. The flowchart then proceeds to an initial mean position step 210.

In initial mean position step 210 processor 38 calculates a mean position of reference distal end 30, and uses this position as a mean position of the heart. The processor uses the reference distal end mean position to evaluate relative positions of distal ends 31 with respect to reference distal end 30. In addition the processor may display a notice on screen 47 indicating to professional 28 that system 20 is tracking distal ends 30 and 31. From step 210, the flowchart returns to step 206, so that steps 206, 208, and 210 repeat iteratively; however, step 209 may not need to be performed after a first iteration has occurred. The reiteration of the steps corresponds to the valid system tracking state illustrated by overlapping lines 106 (FIGS. 3A and 5A).

At a time after at least one of the iterations described above, a situation is assumed where decision step 208 returns a negative value, so that the positions determined by position sensor 36 are no longer constant, do not correspond to the mean position found in step 210, and so that there has been a non-zero change in the mean position of the reference distal end. Such a non-zero change may be indicative of a change in the mean position of the heart, and/or a change in the body coordinate frame of reference.

In this case there is no valid tracking state. Such a situation corresponds to broken arrows 110 and 150 (FIGS. 3A and 5A). Typically in this case, in a loss of valid state tracking step 212 a warning is displayed to professional 28 that tracking has been lost, and the flowchart continues to a second recording step 214.

Second recording step 214 and a second decision step 216 (following step 214) are substantially the same as first recording step 206 and first decision step 208.

If in second decision step 216 the positions do repeat, then the flow chart continues to a subsequent mean position step 218, wherein processor 38 calculates a new mean position of reference distal end 30.

In calculating the new mean position the processor considers the electrical signals from electrodes 32. If the parameter defined in setup step 202 (assumed therein to be the LAT of the signals) has not changed, corresponding to a situation illustrated by FIGS. 3A-3C, then distal end 30 has not moved from the selected site in the coronary sinus. In this case the positions recorded in step 214 are used to calculate a new mean position for reference distal end 30, and the processor assumes the new reference distal end mean position corresponds to the reference site selected in step 204. The processor uses the new reference distal end mean position to evaluate relative positions of distal ends 31 with respect to reference distal end 30.

If in step 218 the LAT of the signals has changed, this corresponds to a situation illustrated by FIGS. 5A-5C. In this case distal end 30 has moved from the selected site in the coronary sinus to a new reference site therein. Substantially as described above with respect to FIGS. 4A-4D, and using the mapping generated in step 209, processor 38 analyzes the signals from electrodes 32 to determine a new reference position of the new reference site within the coronary sinus.

The positions recorded from position sensor 36 in step 214 are used to calculate new mean position coordinates for reference distal end 30, and the processor assumes the new reference distal end mean position corresponds to the new reference site determined from the mapping. Using this correspondence, the processor uses the new reference distal end mean position to evaluate relative positions of distal ends 31 with respect to the new reference site.

If in decision step 216 the positions do not repeat, then the flowchart continues to an invalid tracking state step 220, wherein typically a warning is issued that tracking is not valid. From step 220 the flowchart returns to step 214. Typically, steps 214, 216 and 218 reiterate until the procedure implemented by professional 28 is completed.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for tracking a distal end of a probe in a beating heart, the method comprising the steps of:
    inserting a flexible probe into a living subject;
    positioning a distal end of the probe in a beating heart of the subject at a reference site, the distal end comprising a position sensor configured to generate position signals indicative of a position of the distal end at the reference site, and an electrode configured to be positioned at respective sites on the beating heart to convey electrical signals from the beating heart;
    establishing a valid tracking state for the flexible probe by ensuring there is no change in the position signals over a preset number of heart beats by verifying there is substantially no change in a position of the distal end of the probe over the preset number of heart beats;
    establishing a mean position by recording position signals from the position sensor and electrical signals from the electrode provided there is an established valid tracking state;
    formulating, in response to the position signals, a first indication of a change in the mean position of the beating heart at the reference site within the living subject;
    deriving a second indication of a change in the electrical signals; and
    determining, in response to the first and second indications, a new mean position of the beating heart at the reference site and establishing a new valid tracking state.

2. The method according to claim 1, wherein the change in the mean position of the heart is responsive to a change in the position of the distal end at the reference site.

3. The method according to claim 1, wherein the position of the distal end comprises a mean position of the distal end measured during a preset number of heart beats of the heart.

4. The method according to claim 1, wherein formulating the first indication comprises determining that the position of the distal end does not correspond to the mean position.

5. The method according to claim 1, wherein the second indication is derived in response to determining that the change in the mean position is a non-zero change.

6. The method according to claim 1, wherein the second indication is indicative of no change in the electrical signals.

7. The method according to claim 1, wherein the electrode comprises a plurality of electrodes attached to the distal end, and wherein the plurality of electrodes are configured to convey respective electrical signals from respective sites in the heart.

8. The method according to claim 7, further comprising formulating a mapping between respective parameters of the respective electrical signals and respective positions of the respective sites.

9. The method according to claim 8, further comprising positioning a further distal end of a further probe in the heart, and determining a further position of the further distal end in response to the mapping.

10. The method according to claim 8, wherein the respective parameters comprise respective local activation times of the respective electrical signals.

11. The method according to claim 8, further comprising determining a change in the position of the distal end in response to the mapping.

12. The method according to claim 1, further comprising positioning a further distal end of a further probe in the heart, and determining a further position of the further distal end in response to the new mean position of the heart.

13. An apparatus, comprising:
a flexible probe, having a distal end, configured to be inserted into a living subject and placed at a reference site;
a position sensor comprised in the distal end, configured to generate position signals indicative of a position of the distal end in a heart of the subject at the reference site;
an electrode comprised in the distal end, configured to convey electrical signals from the heart at the reference site; and
a processor, configured to:
establish a valid tracking state for the flexible probe by ensuring there is no change in the position signals over a preset number of heart beats by verifying that there is substantially no change in a position of the distal end of the probe over the preset number of heart beats,
establish a mean position by recording position signals from the position sensor and electrical signals from the electrode provided there is an established valid tracking state,
formulate, in response to the position signals, a first indication of a change in the mean position of the heart within the living subject at the reference site,
derive a second indication of a change in the electrical signals, and
determine, in response to the first and second indications, a new mean position of the heart at the reference site and establishing a new valid tracking state.

14. The apparatus according to claim 13, wherein the change in the mean position of the heart is responsive to a change in the position of the distal end at the reference site.

15. The apparatus according to claim 13, wherein the position of the distal end comprises a mean position of the distal end measured during a preset number of heart beats of the heart.

16. The apparatus according to claim 15, wherein formulating the first indication comprises determining that the position of the distal end does not correspond to the mean position.

17. The apparatus according to claim 13, wherein the second indication is derived in response to determining that the change in the mean position is a non-zero change.

18. The apparatus according to claim 13, wherein the second indication is indicative of no change in the electrical signals.

19. The apparatus according to claim 13, wherein the electrode comprises a plurality of electrodes attached to the distal end, and wherein the plurality of electrodes are configured to convey respective electrical signals from respective sites in the heart.

20. The apparatus according to claim 19, wherein the processor is configured to formulate a mapping between respective parameters of the respective electrical signals and respective positions of the respective sites.

21. The apparatus according to claim 20, and comprising a further distal end of a further probe positioned in the heart, wherein the processor is configured to determine a further position of the further distal end in response to the mapping.

22. The apparatus according to claim 20, wherein the respective parameters comprise respective local activation times of the respective electrical signals.

23. The apparatus according to claim 20, wherein the processor is configured to determine a change in the position of the distal end in response to the mapping.

24. The apparatus according to claim 13, further comprising a further distal end of a further probe positioned in the heart, wherein the processor is configured to determine a further position of the further distal end in response to the new mean position of the heart.

* * * * *